(12) United States Patent
Heikkinen

(10) Patent No.: US 10,272,194 B2
(45) Date of Patent: Apr. 30, 2019

(54) HOLDER FOR PRESSURE INFUSION EQUIPMENT

(71) Applicant: Paavo Heikkinen, Kuopio (FI)

(72) Inventor: Paavo Heikkinen, Kuopio (FI)

( * ) Notice: Subject to any disclaimer, the term of this patent is extended or adjusted under 35 U.S.C. 154(b) by 105 days.

(21) Appl. No.: 14/391,935

(22) PCT Filed: Apr. 11, 2013

(86) PCT No.: PCT/FI2013/000018
§ 371 (c)(1),
(2) Date: Oct. 10, 2014

(87) PCT Pub. No.: WO2013/153254
PCT Pub. Date: Oct. 17, 2013

(65) Prior Publication Data
US 2015/0080803 A1    Mar. 19, 2015

(30) Foreign Application Priority Data
Apr. 12, 2012 (FI) .................................. 20120119

(51) Int. Cl.
*A61M 5/14* (2006.01)
*A61M 5/148* (2006.01)
*A61M 5/142* (2006.01)

(52) U.S. Cl.
CPC .......... *A61M 5/1415* (2013.01); *A61M 5/148* (2013.01); *A61M 5/1424* (2013.01); *A61M 2005/1416* (2013.01)

(58) Field of Classification Search
CPC ...... A61M 5/14244; A61M 2005/1416; A61M 5/1415; A61M 5/148; A61M 5/1483;
(Continued)

(56) References Cited

U.S. PATENT DOCUMENTS 4,090,514 A * 5/1978 Hinck .................. A61M 5/1483
128/DIG. 12
4,529,102 A * 7/1985 Quinn ...................... A61J 1/10
222/456
(Continued)

FOREIGN PATENT DOCUMENTS

FI     8828 U    8/2010
FI     9371 U1   8/2011
(Continued)

OTHER PUBLICATIONS

Federal Service for Intellectual Property, Official Action, Application No. 2014145353/14(073124), mailed Feb. 16, 2017, 14 pages.

*Primary Examiner* — Brandy S Lee
(74) *Attorney, Agent, or Firm* — Ziegler IP Law Group, LLC

(57) ABSTRACT

A pressure solution of an infusion solution holder has a collar that is ergonomically fitted to the shape of the shoulders. The collar includes a pressure tank integrally with the holder and a tank containing the infusion solution. Since the tank containing the infusion solution is located on the patient's shoulders and vertically close to the supply point of the infusion solution, there has to be sufficient pressure in the tank in order for a successful infusion. Therefore, the collar's pressure tank is pressurized by the element, whereby the pressure in the pressure tank is pressing the solution tank and creates the necessary pressure at the time of infusion. The pressurization of the pressure tank is shown in the most cost-effective way by pumping with a manual pressure element, such as a ball pump. Pressurization can also be made, for example, by an electric pump.

14 Claims, 2 Drawing Sheets

(58) Field of Classification Search
CPC .................. A61M 5/152; A61M 5/445; A61M 2209/084; A61M 2209/088; A61M 2205/3633; A61M 5/1424; A61F 5/4405; A61J 1/10; A61J 1/1462; A61J 1/1475; A41D 13/1245; A41D 13/1281
See application file for complete search history.

(56) References Cited

U.S. PATENT DOCUMENTS

| | | | |
|---|---|---|---|
| 5,013,303 A * | 5/1991 | Tamari | A61M 5/1483 128/DIG. 12 |
| 5,147,310 A * | 9/1992 | Giannini | A61M 5/1483 128/DIG. 12 |
| 5,222,946 A * | 6/1993 | Kamen | A61M 5/152 248/121 |
| 5,676,294 A | 10/1997 | Eklund et al. | |
| 5,776,105 A | 7/1998 | Corn | |
| 5,824,000 A * | 10/1998 | Pavlo | A61M 5/1483 604/142 |
| 2005/0252821 A1* | 11/2005 | Azzolini | A61M 5/1483 206/570 |
| 2008/0071242 A1* | 3/2008 | Christoudias | A61J 1/10 604/408 |
| 2008/0296190 A1 | 12/2008 | Marak et al. | |
| 2010/0324532 A1* | 12/2010 | Marak | A61M 5/148 604/507 |

FOREIGN PATENT DOCUMENTS

| | | | |
|---|---|---|---|
| SU | 1762911 A1 | 9/1992 | |
| WO | 9207596 A1 | 5/1992 | |
| WO | WO92/07596 * | 5/1992 | ............ A61M 5/155 |

\* cited by examiner

SECTION A — A

SECTION B — B

SECTION C — C

HOLDER FOR PRESSURE INFUSION EQUIPMENT

FIELD

The present invention relates to the transport of an infusion solution bag, generally used in health care, along with the patient.

BACKGROUND

Currently an infusion bag is transported with a patient by a rolling wheels stand, a so-called the drip tray. From the solution bag placed in the rack can be supplied to the patient's peripheral vessel e.g. nutrient solution, plasma, antibiotic solution etc.

The problem in transporting the rolling wheels stand is that the stand aims to rotate about its vertical axis. Thus, the tube can rotate around the vertical rod, simultaneously blocking the free flow of the solution in the catheter. It is also difficult for the patient to move the stand over doorsteps and moving on stairways and, for example, entering a lift can be extremely difficult. Further, when moving with the stand in corridors, the wheels gather dirt and bacteria.

In the utility model U20100144 as a solution for transporting an infusion bag is used a stand carried on the shoulders. A drawback of the device that is usable as such is that it is difficult to put on. The structure is relatively massive and thus its manufacturing costs are rather high. In addition, the complex structure is difficult to keep clean. Another problem is that the stand is located behind the person's head, and therefore the person cannot see the amount of contents of the bag.

In the utility model U 20110076, a solution for transporting an infusion bag is a rack set onto the shoulders and a chamber structure. A drawback of the solution is that the rack is unstable, which has been aimed to be improved by connecting the rotary straps that wrap around a person's body. The straps, however, complicate putting the rack on the person.

In patent WO9207596 the infusion bag is supported on patient's shoulders in a separate capsule. Pressurization is handled by a separate pressure cuff around the infusion bag. The infusion bag is placed on one of the patient's shoulders and thus there must also be a weight on the other shoulder to balance the holding of objects. In addition, the bracket is supported by separate fastening straps.

SUMMARY

A significant advantage of the infusion solution holder according to the invention compared to the above-mentioned inventions is that the holder (1) is evenly distributed on both sides on the patient's shoulders, wherein carrying the holder (1) is balanced and safe.

In addition, putting on the holder (1) is easy and does not require separate fastening straps around the body.

Further, essential in this invention is that both hands of the patient are free for other purposes, such as opening doors, carrying and lifting goods. As a particular advantage for using the present invention is that the patient can use, for example, crutches or a wheelchair while carrying the holder (1).

With the device according to the new invention, it is possible to avoid the drawbacks in using the infusion solution bags used today. The invention is characterized by what is stated in the claims and an advantageous embodiment of the invention is described by means of the enclosed FIGS. 1 and 2.

BRIEF DESCRIPTION OF THE DRAWINGS

Next, the invention is described in more detail by referring to the attached drawings, wherein.

DETAILED DESCRIPTION

Figure 1:
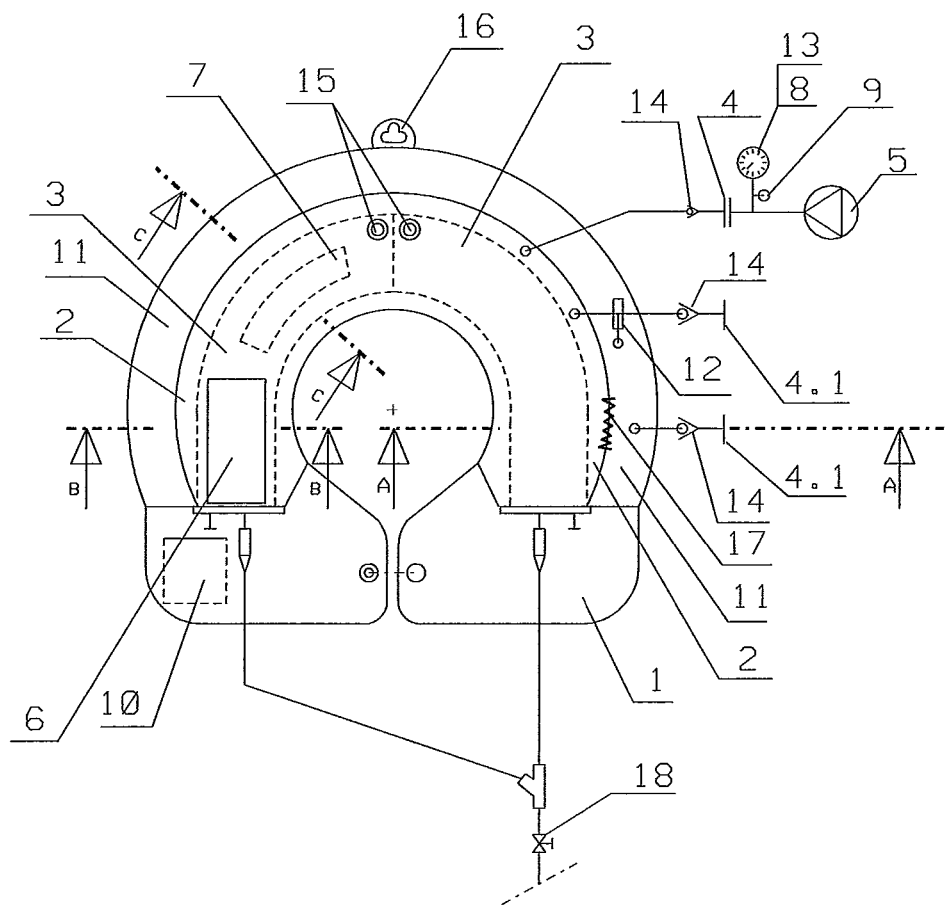
FIG. 1 shows a principal drawing of an infusion bag with an embodiment of the infusion solution holder according to invention seen from above, and FIG. 2 show the sections A-A, B-B and C-C of the infusion bag according to FIG. 1.

In FIG. 1 the pressure infusion solution holder (1) has a collar (2.3) that is ergonomically designed to the shape of the shoulders and a suitably in connection with the collar (2, 3) constructed solution tank (3) comprising the infusion solution and a pressure tank (2). Since the infusion solution tank (3) is located on the patient's shoulders and vertically close to the supply point to the vine, the tank (3) must have a sufficient pressure to have success for infusion. Therefore, the pressure tank (2) of the collar (2.3) is pressurized e.g. with compressed air, at which time pressure compresses the solution tank (3) and creates the necessary pressure for infusion.

In the pressure tank (2) of the collar (2.3) pressurization is in this invention shown in the most cost-effective manner, i.e. pressure is pumped by a manual pressurization element (5) such as a ball pump. Pressurization can also for example be made by an electric pump. Pressurization element (5) is releasably connected to the pressure tank (2) by an adapter (4) and pressure is controlled by a pressure gauge (8).

When the solution decreases in the solution tank (3), pressure also drops in the pressure tank (2), and if the pressure drops below the required pressure value, the pressure must be returned to the desired value and therefore there is a container structure (11) in the holder (1), which container structure (11) is over pressurized compared with the pressure tank (2). After the pressure drops in the pressure tank (2), there is a pressure regulator (12) between the pressure tank (2) and the container structure (11), which allows overpressure of the container structure (11) to discharge to the pressure tank (2), and increases the pressure to the desired level.

In this case the pressurization element (5) does not necessarily need to be transported along with the patient. Instead of a pressure regulator (12), or along with it, is used a seal (17), the breaking of which allows the overpressure of the container structure (11) to discharge to the pressure tank (2) in the same way as when using the pressure regulator (12). The section A-A in FIG. 2 discloses the seal (17) located between the pressure tank (2) and the container structure (11).

From the bottom of the collar (2, 3) the tubes are connected to connector/connectors, from where the infusion solution flows into the peripheral vein via e.g. a controller (18). In the holder it is in different applications possible to add additional components such as pockets (10) and/or fittings, for example, for transporting antibiotic solution bags or for locating physiological measuring devices.

Temperature of the solution can be maintained by a thermal element (7) located in the holder (1).

Figure 2:
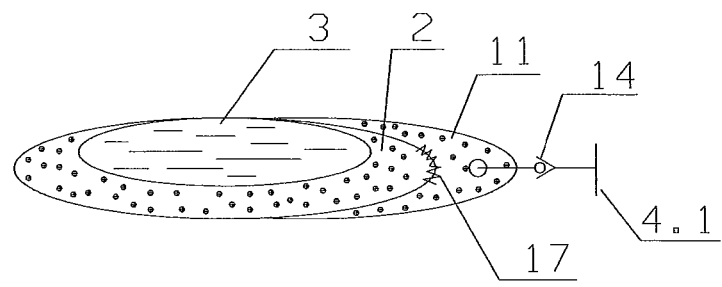
Figure 2:
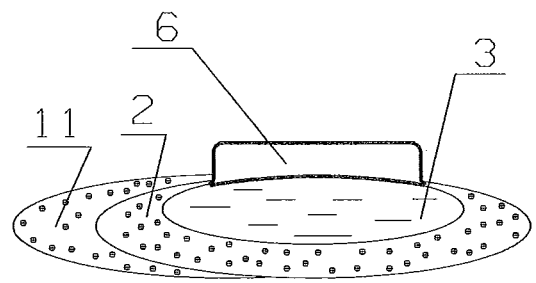
Figure 2:
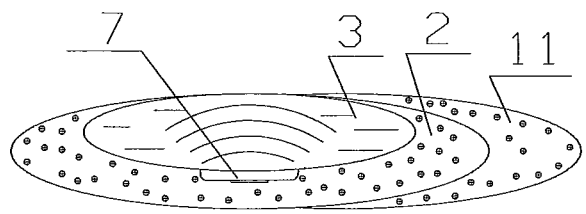

In FIG. 2 the cross section C-C shows the thermal element (7) placed in the immediate vicinity of the solution tank (3)

and it is hermetically separated from it. The thermal element (7) can also be located in different places but in such way that the effect of the thermal element on the solution in the solution tank (3) is sufficient.

There is a space (6) in the holder (1) for a separate infusion bag. In FIG. 2 in the section B-B the space (6) is positioned near the pressurized solution tank (3), but it can also be located in a different place, however, in such way that the pressure effect of the pressure tank (2) is conveyed into the infusion bag in the space (6).

A separate infusion bag can be attached to the holder, instead of the space (6), also with a separate fastening element, such as adhesive tape or a mechanical fastening.

the tank/tanks (3) are refillable e.g. through an inlet (15).

By the fastening (16) the holder (1) of the infusion solutions can be positioned e.g. on the drip tray in a traditional hospital bed or on other similar fastening device.

Putting the holder (1) on can be compared to e.g. putting on a cloth collar and that is why putting the holder on is relatively easy for persons of all ages.

The invention is not limited to the advantageous embodiment shown above but it is possible to vary within the scope defined in the claims.

The invention claimed is:

1. A holder arranged for supporting pressure infusion equipment on a patient's shoulders, comprising a pressurization element, and a collar, ergonomically adaptable to a shape of the shoulders, which is constructed of:
    at least one solution tank built into the collar;
    at least one pressure tank built into the collar and at least partially surrounding the solution tank;
    an over pressured container structure built into the collar and at least partially surrounding the at least one pressure tank; and
    a pressure regulator connected in line between the over pressured container structure and the at least one pressure tank to allow overpressure of the container structure to discharge through the pressure regulator to the pressure tank when pressure in the pressure tank drops.

2. The holder according to claim 1, wherein the holder comprises a pressure limit value indicator.

3. The holder according to claim 1, wherein the holder has at least one space for a separate infusion bag.

4. The holder according to claim 1, wherein the holder has at least one or more pockets.

5. The holder according to claim 1, wherein the holder has at least one thermal element to maintain a temperature of a solution in the at least one solution tank.

6. The holder according to claim 1, wherein the at least one solution tank is made refillable through an inlet.

7. The holder according to claim 1, further comprising an adapter releasably connecting the pressurization element to the at least one pressure tank.

8. A holder arranged for supporting pressure infusion equipment on a patient's shoulders, comprising a pressurization element, and a collar, ergonomically adaptable to a shape of the shoulders, which is constructed of:
    at least one solution tank built into the collar;
    at least one pressure tank built into the collar and at least partially surrounding a solution tank;
    an over pressured container structure built into the collar and at least partially surrounding the at least one pressure tank; and
    a seal in line between the over pressured container structure and the at least one pressure tank that, when broken, allows overpressure of the container structure to discharge through the seal to the pressure tank.

9. The holder according to claim 8, wherein the holder comprises a pressure limit value indicator.

10. The holder according to claim 8, wherein the holder has at least one space for a separate infusion bag.

11. The holder according to claim 8, wherein the holder has at least one or more pockets.

12. The holder according to claim 8, wherein the holder has at least one thermal element to maintain a temperature of a solution in the at least one solution tank.

13. The holder according to claim 8, wherein the at least one solution tank is made refillable through an inlet.

14. The holder according to claim 8, further comprising an adapter releasably connecting the pressurization element to the at least one pressure tank.

* * * * *